(12) United States Patent
McInnis et al.

(10) Patent No.: US 6,602,985 B1
(45) Date of Patent: Aug. 5, 2003

(54) EXTRACTION OF ZEIN PROTEIN FROM GLUTEN MEAL

(75) Inventors: Jerel McInnis, Cordova, TN (US); Qingnong Tang, Saskatchewan (CA)

(73) Assignee: Lurgi PSI, Inc., Memphis, TN (US)

( * ) Notice: Subject to any disclaimer, the term of this patent is extended or adjusted under 35 U.S.C. 154(b) by 0 days.

(21) Appl. No.: 09/501,836

(22) Filed: Feb. 10, 2000

(51) Int. Cl.⁷ .............................................. C07K 14/415
(52) U.S. Cl. ...................... 530/373; 530/376; 530/422; 530/424; 530/427
(58) Field of Search ................................ 530/373, 376, 530/422, 424, 427

(56) References Cited

U.S. PATENT DOCUMENTS

| | | | |
|---|---|---|---|
| 456,773 A | 7/1891 | Osborne | |
| 696,156 A | 3/1902 | Wulkan | |
| 1,992,122 A | 2/1935 | Hansen et al. | 91/68 |
| 2,105,760 A | 1/1938 | Swallen | 87/28 |
| 2,120,946 A | 6/1938 | Swallen | 87/28 |
| 2,229,870 A | 1/1941 | Pearce | 260/123 |
| 2,272,488 A | 2/1942 | Swallen | 260/123 |
| 2,287,649 A | 6/1942 | Swallen | 260/123 |
| 2,332,356 A | 10/1943 | Swallen et al. | 260/123 |
| 2,354,393 A | 7/1944 | Manley et al. | 260/123 |
| 3,370,054 A | 2/1968 | Loew | 260/123 |
| 3,535,305 A | 10/1970 | Carter et al. | 260/123 |
| 3,676,365 A * | 7/1972 | Shirai | 252/422 |
| 3,962,335 A | 6/1976 | Kumar | 426/574 |
| 3,963,575 A | 6/1976 | Bulich | 195/31 R |
| 4,624,805 A | 11/1986 | Lawhon | 530/376 |
| 4,716,218 A | 12/1987 | Chen et al. | 530/372 |
| 5,410,021 A | 4/1995 | Kampen | 530/372 |
| 6,017,753 A * | 1/2000 | Johnson et al. | 435/276 |
| 6,113,975 A * | 9/2000 | Grace et al. | 426/656 |
| 6,217,664 B1 * | 4/2001 | Baniel | 127/53 |

OTHER PUBLICATIONS

Dombrink–Kurtzman Journal of Cereal Science 19, 57, 1994.*
Bajpai Indian J. Chem. Sect A Inorg Bio–Inorg Phys Theor. Anal. Chem. 36A(9), 783–784, 1997.*

* cited by examiner

*Primary Examiner*—Christopher S. F. Low
*Assistant Examiner*—David Lukton
(74) *Attorney, Agent, or Firm*—Fulbright & Jaworski L.L.P.

(57) ABSTRACT

Zein is recovered from gluten meal prepared by wet milling procedures by washing the gluten with clean water to remove water-soluble components; separating the water-soluble components and recovering the water-insoluble components; extracting the water insoluble components with hydrous ethanol solvent to extract zein; recovering the crude zein extract; treating the crude zein extract with an adsorbent that adsorbs at least one of color, odor, oil and fatty acid; and to yield a purified zein extract.

3 Claims, 1 Drawing Sheet

EXTRACTION OF ZEIN PROTEIN FROM GLUTEN MEAL

FIELD OF THE INVENTION

This invention provides a process for recovering zein protein from gluten meal prepared from corn or other gluten bearing grains. The process of the invention is designed for implementation as an add-on module in existing wet milling alcohol production plants or as an integrated unit at new alcohol production facilities.

BACKGROUND AND SUMMARY OF THE INVENTION

Zein is a hydrophobic protein found corn, millet, rice and other plants. Zein has many commercial uses including the manufacture of edible food packaging, edible films, biodegradable plastic resins, and tablet coating compounds. In U.S. corn wet milling facilities, zein is typically concentrated into a co-product fraction commercially referred to as corn gluten meal (CGM). CGM is commonly used as a protein source in animal food products without any attempt to recover the more valuable zein protein the CGM contains.

There are many known techniques for recovering zein as well as other natural ingredients such as oil, from corn. U.S. Pat. No. 4,716,218 to Chen et al. describes a process for producing grain oil, dehydrated alcohol, grain protein such as zein and starch utilizing ethanol extraction. The process for the production of grain oil and dehydrated alcohol by cracking the grain; drying the grain to a moisture content sufficiently low to enable the grain to dehydrate an ethanol solution to greater than 90% ethanol, while simultaneously extracting the grain oil from the dried grain with an ethanol solution of greater than 90% ethanol, and recovering the grain oil and dehydrated alcohol from the extractant. In a preferred embodiment, cracking the grain, drying the grain to a moisture content sufficiently low to dehydrate an ethanol solution of greater than 90% ethanol while simultaneously extracting oil from the dried grain with a first ethanol solution of greater than 90% ethanol, recovering oil and dehydrated alcohol from the first extractant, extracting grain protein from the residue of step with a second ethanol solution wherein the ethanol concentration is that which maximizes the protein solubility, recovering the protein from the second extractant, recovering starch from the residue of step.

U.S. Pat. No. 5,410,021 to Kampen describes and claims a process for recovering protein, protein isolate or starch from cereal grains such as corn that utilizes wet-attrition milling to break the protein-starch bonds while leaving the starch granulates intact. Kampen's process includes recovering protein from cereal grains containing starch and protein bound into a matrix by the grinding said grains to a particle size appropriate for introduction to a wet attrition mill; defatting said grain; wet attrition milling particles of said grain to a size sufficiently small to break the bond between starch and protein, then extracting the broken bond protein from the starch with at least one solvent, then separately the resulting high liquid content portion containing the extracted protein from the resulting high solids content portion containing the starch, and then subjecting the high liquid content portion containing the extracted protein to continuous cross-flow microfiltration with inorganic membranes for isolating the protein constituent, concentrating the protein constituent into a dry power.

U.S. Pat. Nos. 5,254,673 and 5,580,959 to Cook disclose extraction of zein, zein bodies, glutelins or destarched corn gluten from corn gluten meal by enzymatic starch hydrolysis with an amylase, alkaline treatment, alcohol washing and alcohol extraction to yield a starch-free, deflavored and decolored zein. The method includes the steps of removing color and flavor impurities from the gluten by treating corn gluten with alkali to remove fatty acids and corn oils contained therein and then with an aqueous alcoholic solvent having a concentration which does not substantially extract zein, zein bodies and glutelins therefrom, thereafter changing the concentration of the alcoholic solvent to a concentration sufficient to separate the gluten into decolored and deflavored zein or zein bodies and glutelin fractions.

U.S. Pat. No. 4,486,353 to Matzuzaki et al. discloses a specific process of extracting vegetable oil and fats from oleaginous raw material such as corn gern by obtaining flakes having a moisture content of from 0.7 to 10 weight % from an oleaginous raw material, said flake being characterized by the absence of an impervious outer hull or coat; contacting said flakes with an ethanol solution containing not less than 90 weight % ethanol at a temperature in the range from 70° C., to the boiling point of said ethanol solution, thereby obtaining a miscella, cooling said miscella, thereby obtaining vegetable oil or fat or both, and a separate defatted miscella; drying said defatted miscella with a molecular sieve material having a pore size from 3 Å to 4 Å, thereby obtaining a second ethanol solution wherein said second ethanol solution contains less than 7 weight % water; and using said second ethanol solution as the ethanol solution of said contacting step in a second extraction.

U.S. Pat. No. 5,773,076 to Liaw et al. is directed to a wet milling process in which gluten is recovered from steep water by membrane filtration and is then incorporated into a corn gluten meal product. The process of recovering insoluble gluten protein from steep water in a corn wet milling process includes steeping corn kernels in an aqueous solution that comprises gluten wash water, thereby producing steep water which contains insoluble gluten protein; membrane filtration of the steep water, thereby producing a retentate which has a higher concentration of the insoluble gluten protein than the original steep water; reducing the water content of the retentate; and incorporating the remaining retentate into a corn gluten meal product.

U.S. Pat. No. 5,342,923 to Takahashi et al. describes a process for refining zein with a high purity acetone solution by dispersing a solution containing crude zein into a solution comprising acetone in which said zein is insoluble; thereby precipitating a zein component as porous solids; separating said porous solids; and drying said solids. U.S. Pat. No. 5,510,463 to Takahaski et al. discloses a process for producing zein wherein zein and pigment components are extracted from a corn gluten meal that has been treated with a $C_5$–$C_9$ hydrocarbon solvent. The zein is extracted by subjecting the treated corn gluten meal with a solvent having 91–96% by volume ethanol. The zein and the pigment components are then separated from the extract solution. Oil and fat components and pigment components may be extracted prior to the zein extraction steps.

U.S. Pat. No. 5,367,055 to Takahashi et al. discloses a process for treating a zein containing material to decrease inherent color and smell and to obtain zein by contacting the material with an aqueous acetone solution having an acetone solution which "causes almost no dissolution" of the zein compound. The process includes the steps of contacting the zein-containing material with (1) a 80–100% (V/V) acetone solution at a temperature of 25–60° C., or (2) a 70–80% (V/V) acetone solution at a temperature of 25–40° C., and separating the resulting solid from the solution.

U.S. Pat. No. 4,624,805 to Lawhon describes a process for recovering food grade protein from agricultural commodities, e.g., corn, prior to alcohol production. The process includes the steps of obtaining a suitable agricultural commodity in a form suitable for extraction of protein; extracting protein from said agricultural commodity with an alkali solution which forms a dispersion with said agricultural commodity; separating the dispersion into a solids fraction and a liquids fractions, said liquids fraction containing extracted protein; removing the protein from said liquids fractions by ultrafiltration using a membrane having a molecular weight cutoff between about 10,000 and about 30,000 daltons; and utilizing said solids fraction for alcohol production.

The present invention provides an economical process for extracting zein from gluten prepared from corn or other grains at a wet milling facility that produces ethanol. The process incorporates a water washing step, preferably using counter current techniques, to remove water-soluble components from wet or dry gluten. The water washing step is immediately followed by extraction with an aqueous ethanol solvent to remove the zein protein fraction of the gluten. The insoluble gluten components such as starch and cellulose are then separated from the solution, e.g. by centrifugation or filtration. The starch-bearing solids may then be hydrolyzed to simple sugars by acid conversion technology and used as feed for an existing fermentation system.

The alcoholic zein solution is treated with activated carbon or another adsorbent to remove at least one of color, odor, and other undesirable components from the zein. When activated carbon is used as the adsorbent, the resulting zein solution is clear. This solution is then preferably filtered and dried, e.g, by spray drying to obtain a high-purity zein product that is suitable for use, e.g. in producing edible films and biodegradable plastic resins. The filtered zein solution can also be directly incorporated in the manufacture of other products without drying, e.g, for direct use in a process for preparing biodegradable polymers.

DETAILED DESCRIPTION OF INVENTION

Figure 1:
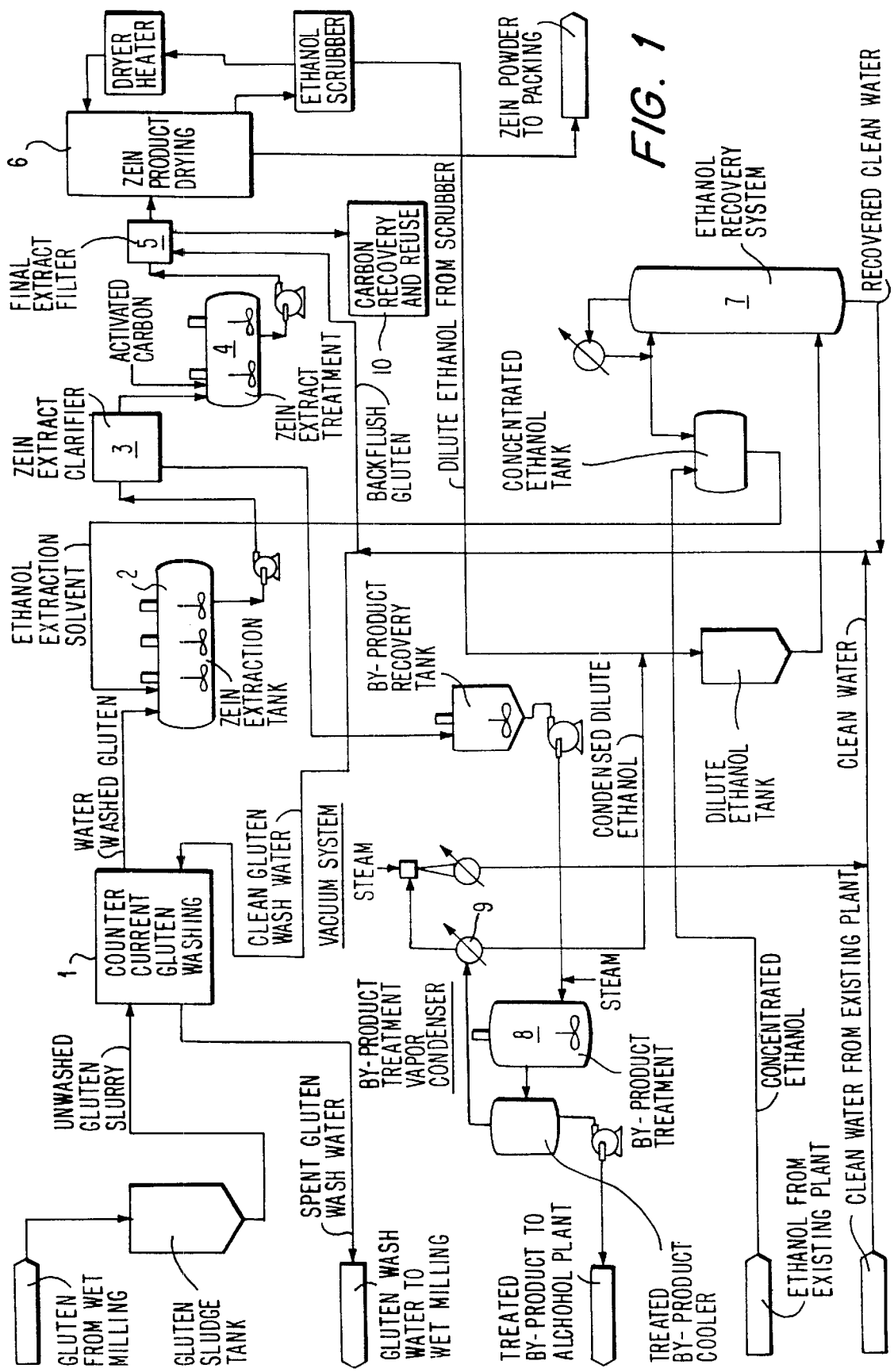
FIG. 1 is a process flow diagram of a particularly preferred embodiment of the invention.

In a preferred embodiment of the invention, the process begins by washing wet corn gluten from a corn wet milling operation with water. The process of the invention also contemplates the use of dry corn gluten meal as a feed, but the use of wet gluten provides an economic advantage by eliminating the gluten drying step, a significant commercial advantage. The process of the present invention will typically be applied as an add-on module to an existing wet milling facility that produces ethanol, but may be an integral part of a new wet milling facility as well.

Water is used to wash the feedstock and remove water-soluble components from the corn gluten. Counter current washing is preferred because of the enhanced efficiency provided by this method. Zein is then extracted from the washed gluten using a 70–75 wt. % ethanol solution to dissolve the zein. The crude zein extract is clarified, e.g., by filtration or centrifugation, to remove visible suspended solids.

After clarification, a suitable amount of activated carbon or other adsorbent which removes at least one of color, odor, or other undesirable components is added to the alcoholic zein solution to remove at least a portion of the component. Typically, 0.1 to 5% by weight of adsorbent based on the total solution is added, however this will vary with the properties of the selected adsorbent, the desired purity of zein to be produced, the amount of impurities in the gluten feedstock, and other factors known to those in the art. Thus, the amount of adsorbent added may range from 0.1 to 10 % by weight of the total solution based on the aforementioned factors and other considerations. The zein extract/adsorbent mixture is then filtered to remove the adsorbent and any adsorbed impurities, yielding a refined zein solution. The refined zein solution may then be used to prepare an end product, or may be dried to recover the purified zein in dry powder form. The dried zein product typically contains 85–99% by weight zein. It should be noted that the final product may also contain impurities which may include proteins other than zein.

The by-products of the process can be recovered for use as fermentation feed stock. Any residual ethanol in the recovered by-product is preferably collected, e.g., by using surface contact condensation of flash cooling vapors. The adsorbent is preferably regenerated using known techniques for reuse in the process. Recovery of all dilute ethanol streams by reconcentration is preferred so that the ethanol can be reused in the process increasing efficiency. Additional detail is provided in the items below and in the attached process schematic, FIG. 1, which sets forth a particularly preferred embodiment of the invention.

Referring to FIG. 1, corn gluten from a wet milling operation is continuously fed to washing unit 1 to undergo a series of counter current water washing and dewatering steps. During washing, water-soluble components of the gluten are removed from the water insoluble zein-bearing fraction. Counter current washing with water greatly reduces the amount of water that would be required by batch washing. Any type of water may be used e.g., deionized, distilled, well water, or tap water. Alternatively, recycled process condensates are used as a water source. The spent wash water along with the water-soluble components is preferably routed back to the wet milling operation for use in the process.

The washed gluten cake is then fed to an extractor 2 for zein extraction. During the extraction process, hydrous ethanol solution is used as the solvent to extract zein from the washed cake. Ethanol used in the operation within the tank may range from 40 to 90% by weight ethanol, but the best extraction results are obtained at a concentration of 70–75% by weight ethanol. Extraction may be performed in the range of 35 to 80° C., but the best results are obtained at 50° C. The washed cake and ethanol are held in the extraction tank for 10 to 120 minutes to complete dissolution of the zein protein. The crude zein extract is then routed to a clarification unit for removal of suspended solids.

The crude zein extract is preferably clarified e.g., by centrifugation or filtration 3, to remove gluten components that are not soluble in hydrous ethanol. Typical insoluble components include starch, cellulose, and protein components other than zein. The separated solid material is routed to by-product recovery for additional treatment as discussed below.

The clarified zein extract is routed to extract treatment tank 4 for removal of additional impurities by treatment with an adsorbent, preferably activated carbon, to remove at least a portion of at least one of such impurities such as lipids, color, and odor, which are undesirable in the finished zein product. A number of adsorbents can be used, such as powdered activated carbon, granular activated carbon, activated charcoals, bentonite bleaching clays, and structured polymeric resins. Any resin having similar adsorption properties may be selected and used in refining the zein solution. A sufficient amount of absorbent will be used to remove the desired amount of impurity to yield the desired zein product. In the preferred embodiment, activated carbon is used as the adsorbent. The clarified zein extract is intimately mixed with the adsorbent and is then retained in a treatment tank for about 10 minutes to about 2 hours, preferably 45–60 minutes to allow impurities to be adsorbed and removed from the solution. In certain embodiments, the adsorbent is contained in an absorption column and the crude zein solution is passed through the column to remove the adsorbable impurities. Afterwards, the adsorbent/extract mixture is discharged from treatment tank 4 and routed to filter 5 to remove any adsorbent and adsorbed impurities. The absorbent is then preferably regenerated for reuse in the process.

The resultant purified zein solution may then be directly used to make end products, or may optionally be routed to a dryer 6 to yield a dry zein powder. For powder forms, the purified zein extract is preferably spray dried to simultaneously remove the ethanol and excess water and yield the final zein powdered product. For both safety and product quality concerns, the drying step should be conducted under non-flammable conditions, e.g., by nitrogen blanketing.

Zein powder is the preferred form of the product and can be of any desired purity depending on the intended use. A preferred product is a white to near-white zein powder containing 4 to 6 percent by weight water and having a protein content of 85–99% by weight on a dry weight basis.

When dried in a spray dryer, the dry zein powder is separated from the dryer exhaust vapors and routed to packaging for commercial sale. The dryer exhaust is a mixture of ethanol vapor and other gases and is preferably routed to a condensing scrubber where most of the alcohol vapor and some of the water vapor are condensed to liquid hydrous ethanol. Remaining gases from the scrubber are routed to the dryer and are heated and reused in the dryer as the drying medium.

Condensed ethanol streams from drying and by-product treatment operations may be reconcentrated and reused in the process by e.g., being fed into single-column distillation unit 7 which concentrates the diluted alcohol feed to 85 to 93 percent by weight ethanol that is reused in the zein extraction operation. Excess water from the dilute ethanol streams is discharged from the bottom of the column and recycled into the process.

The by-product from the clarification process contains starch along with other components that are not soluble in hydrous ethanol. This by-product material is preferably recovered by mixing with dilute mineral acid and heating in pressure tank 8 to hydrolyze the starch fraction to simple sugars that can be fermented. Hydrolysis converts the material to a thinned slurry that can be pumped back to the ethanol plant for use as fermentation feed. The thinned slurry is transported to a flash cooler and is flash-cooled to 75–95° C. by applying a vacuum as indicated in FIG. 1. Condenser 9 is operatively positioned between the flash cooler and the vacuum source. The flash-cooled slurry is then recycled to the alcohol production facilities for recovery or reuse.

DETAILED DESCRIPTION OF PREFERRED EMBODIMENTS

EXAMPLE 1

Preparation of Zein Without Carbon Treatment

Distilled water was heated to 50° C. Dry corn gluten prepared by wet milling was added to the distilled water to form a smooth, fluid suspension. The mixture was held at 50° C. for one hour to allow dissolution of water-soluble components. The mixture was then filtered to separate the water-soluble components from the insoluble components. Of the original solids added, about 94% by weight were recovered from the water washing step. The water washed and dried corn gluten solids were then mixed with 70% by weight ethanol solution at 50° C. to form a fluid suspension. The mixture was held at 50° C. for one hour to allow the zein protein component to dissolve. After one hour, the mixture was centrifuged to separate the liquid zein extract from the remaining solids that are not soluble in hydrous ethanol.

The centrifuged zein extract was dried in a vacuum pan oven at 40° C. The dried product was milled to produce a yellow powder product that contained about 5% moisture and had a protein content of 95% on an as-is basis. The yellow powder readily formed a clear, light yellow solution when mixed with 90% by volume ethanol.

EXAMPLE 2

Preparation of Near-White Zein

Dry corn gluten meal was added to distilled water at a temperature 50° C. to form a fluid suspension. The gluten and water mixture was held at 50° C. for one hour to allow water-soluble components to dissolve. The mixture was then filtered to separate the water-soluble components from the components not dissolved by water. The water washed solids were dried before further processing. After water washing, the dried corn gluten solids were mixed with a 70% by weight ethanol/water solution at 50° C. The mixture was held at 50° C. for one hour to allow the zein protein fraction of the gluten to dissolve. After one hour, the mixture was centrifuiged to separate the liquid zein extract from the remaining ethanol insoluble components.

Powdered activated carbon was mixed into the clarified zein extract and the mixture was held at 50° C. for one hour to allow impurities to be adsorbed by the carbon. After one hour, the mixture was filtered to remove the powdered carbon. The filtered extract was dried in a vacuum pan oven at 40° C.

The dried product was milled to produce a near-white powder product that had a protein content of 96% by weight on an as is basis. The powdered product readily formed a clear solution when mixed with 90% by volume ethanol.

U.S. patent application Ser. No. 09/469,032 filed on Dec. 21, 1999 and all references cited herein are incorporated by reference in their entirety.

Other embodiments of the invention will be apparent to those skilled in the art and are meant to be encompassed by the claims attached hereto.

We claim:

1. A process for preparing spray-dried zein protein from corn gluten comprising:

(a) washing corn gluten with water to remove water-soluble components and recover the water-insoluble components containing the zein;

(b) extracting the water-insoluble components with 40–90% hydrous ethanol solvent to extract zein and form a crude zein liquid composition;

(c) removing insoluble components from said crude zein liquid composition to form an intermediate zein-containing liquid composition;

(d) treating the intermediate zein-containing liquid composition with activated carbon for a time and under conditions effective to adsorb at least one of color, odor, oil and fatty acid to form an activated carbon-treated, zein-containing liquid composition;

(e) removing the activated carbon and any adsorbed impurities from the activated carbon-treated, zein-containing liquid composition to yield a purified zein extract; and (f) spray drying the purified zein extract to yield spray-dried zein protein.

2. The process of claim 1, wherein the hydrous ethanol extraction step is conducted at a temperature of 35 to 80° C.

3. The process of claim 1, wherein the corn gluten is either wet or dry.

* * * * *